United States Patent
Obukowicz et al.

(12)

(10) Patent No.: US 6,340,705 B1
(45) Date of Patent: *Jan. 22, 2002

(54) USE OF α-LINOLENIC ACID METABOLITES FOR TREATMENT OR PREVENTION OF CANCER

(75) Inventors: Mark Obukowicz, Kirkwood; Ayman Kabakibi, Creve Coeur; Susan L. Green, St. Ann; Lisa M. Olson, Richmond Heights, all of MO (US); Julie Lindemann, El Cerrito, CA (US)

(73) Assignee: Monsanto Technology, LLC, St. Louis, MO (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/393,790

(22) Filed: Sep. 10, 1999

(51) Int. Cl.⁷ .............................................. A61K 31/20
(52) U.S. Cl. ...................................... 514/560
(58) Field of Search ........................................ 514/560

(56) References Cited

U.S. PATENT DOCUMENTS

| | | | | |
|---|---|---|---|---|
| 5,158,975 A | * | 10/1992 | Guichardant et al. | 514/560 |
| 5,178,873 A | * | 1/1993 | Horrobin et al. | 424/422 |
| 5,562,913 A | | 10/1996 | Horrobin | 424/401 |
| 5,886,037 A | | 3/1999 | Klor et al. | 514/546 |
| 5,763,484 A | * | 6/1999 | Horrobin | 514/560 |
| 5,925,669 A | * | 7/1999 | Katz et al. | 514/449 |

FOREIGN PATENT DOCUMENTS

| | | |
|---|---|---|
| EP | 0 440 307 | 8/1991 |
| WO | 97/39749 | 10/1997 |

OTHER PUBLICATIONS

"Japanese bionews: Sagami Chemical Research Institute Samgami Chemical Research: Finds that docosapentaenoic acid amy prevent allergic conditions" Genetic Engineering News, (Apr. 15, 1992) p. 21 ISSN:1270–6377.*
Whelan, J., et al., Lipids, vol. 26 (1991) 119–126.
Hwang, D.H., et al., J. Nutr., vol. 118 (1988) 427–437.
Braden, L.M., et al., Lipids, vol. 21 (1986) 285–288.
Reddy, B., et al., Cancer Res., vol. 46 (1986) 3367–3370.
Minoura, T., et al., Cancer Res., vol. 48 (1988) 4790–4794.
Nelson, R.L., et al., Nutr. Cancer, vol. 11 (1988) 215–220.
Reddy, B., et al., Cancer Res., vol. 48 (1988) 6642–6647.
Li, B.Y., et al., J. Lipid Res., vol. 35 (1994) 1869–1877.
Lee, D., et al., J. Nutr., vol. 123 (1993) 1808–1917.
Paulsen et al., Carcinogenesis, vol. 18 (1997) 1905–1910.
Oshima et al., Carcinogenesis, vol. 16 (1995) 2605–2607.
Moser, A.R., et al., Eur. J. Cancer, vol. 31A (7–8) (1995) 1061–1064.

* cited by examiner

Primary Examiner—Theodore J. Criares
Assistant Examiner—J. Kim
(74) Attorney, Agent, or Firm—Fitzpatrick, Cella, Harper & Scinto (57) ABSTRACT

Cancer in a mammal can be treated or prevented by administering to a mammal in need thereof a cancer inhibiting amount of metabolite(s) of α-linolenic acid, such as stearidonic acid (18:4 n-3), eicosatetraenoic acid (20:4 n-3), docosaptentaenic acid (22:5 n-3) and mixtures thereof, especially metabolites including stearidonic acid.

23 Claims, 8 Drawing Sheets

USE OF α-LINOLENIC ACID METABOLITES FOR TREATMENT OR PREVENTION OF CANCER

FIELD OF THE INVENTION

This invention relates to the use of α-linolenic acid metabolites for the treatment of cancer. More specifically, this invention relates to the use of stearidonic acid for treatment or prevention of cancer, particularly epithelial cell cancers such as, colon cancer, breast cancer, lung cancer and prostate cancer.

BACKGROUND OF THE INVENTION

There are two types of essential fatty acids (EFAs), the n-3 (or ω-3) type derived from α-linolenic acid and the n-6 (or ω-6) type derived from linoleic acid. The starting polyunsaturated fatty acids (PUFAs) of these metabolic pathways (i.e., α-linolenic acid and linoleic acid) cannot be produced in the body, and therefore must be obtained in the diet. The desaturation and elongation pathways for the n-3, n-6 and n-9 PUFAs are shown below.

An important factor providing evidence that dietary fats can have a significant effect on tumorigenesis is data which suggest that the type of fat in the diet may be as important as the quantity of fat in mediating tumor promotion. In this regard, a great deal of attention has been focused on PUFAs. Although the precise mechanisms responsible for the effects of PUFAs are unknown, it has been suggested that PUFA effects are mediated through arachidonic acid, possibly via prostaglandins, HETEs and leukotrienes.

It has long been known that dietary n-3 PUFAs are very effective in depressing tissue arachidonic acid content, and that the long chain n-3 PUFAs are more effective than α-linolenic acid. Whelan, J., Broughton, K. S. and Kinsella, J. E., Lipids, Vol. 26, 119–126 (1991); Hwang, D. H., Boudreau, M. and Chanmugan, P., J. Nutra., Vol. 118, 427–437 (1988). In addition, diets containing n-3 PURAs, particularly those found in fish oils (i.e., eicosapentaenoic acid (EPA) and docosahexaenoic acid (DHA)), are reported to diminish tumor formation and promotion, and n-3 PURA intake is negatively correlated with chemically-induced tumorigenesis. Braden, L. M. and Carroll, K. K., Lipids 21:285–288, 1986; Reddy, B., and Maruyama, H., Cancer Res. 46:3367–3370, 1986; Minoura, T., Takata, T., Sakaguchi, M., Takada, H., Yamamura, M., Hicki, K. and Yamamoto, J., Cancer Res. 48:4790–4794, 1988; Nelson, R. L., Tanure, J. C., Andrianopoulos, G., Sourza, S. and Lands, W. E. M., Nutr. Cancer 11:215–220, 1988; Reddy, B. and Sugle, S., Cancer Res., 48:6642–6647, 1988.

Tissue arachidonic acid content is correlated with eicosanoid biosynthesis. Li, B. Y., Birdwell, C. and Whelan, J., J. Lipid, Res., Vol. 5, 1869–1877 (1994). Eicosapentaenoic acid levels in colonic mucosal phospholipids are negatively associated with indices of cell proliferation. Lee, D.-Y. K., Lupton, J. R., Aukema, H. M. and Chapkin, R. S., J. Nutr., Vol. 123, 1808–1917 (1993). Conversely, arachidonic acid content in colonic mucosal phospholipids is associated with higher indices of cell proliferation. Lee, D.-Y. K., Lupton, J. R., Aukema, H. M. and Chapkin, R. S., J. Nutra., Vol. 123, 1808–1917 (1993).

More recently, Paulson et al. showed that a fish oil derived concentrate of eicosapentaenoic acid (EPA) and docosahexaenoic acid (DHA) decreased intestinal polyp formation and growth in Δ716 Apc knockout Min/+ mice. Carcinogenesis, Vol. 18, 1905–1910 (1997). Similarly, Oshima et al. showed that dietary DHA-ethyl ester reduced intestinal polyp development in Δ716 Apc knockout Min/+ mice. Carcinogenesis, Vol. 18, 2605–2607 (1995). Moser, A. R., Lougo, C., Gould, K. A., McNeley, M. K., Shoemaker, A. R., Dove, W. F., Eur. J. Cancer, 31A(7–8), 1061–1064 (1995).

European patent application No. 0 440 307 A2 discloses compositions for use in the treatment of breast cancer. The disclosed compositions contain one or more metabolites of α-linolenic acid and one or more metabolites of linoleic acid.

International Application No. 97/39749 describes methods for the prevention and treatment of cachexia and anorexia. Cachexia and anorexia are said to be common conditions among cancer patients whose diseases have progressed to metastatic cancer. The disclosed methods involve administering to an individual an oil blend containing n-6 and n-3 fatty acids, a source of amino-nitrogen which includes branched-chain amino acids, and an antioxidant component.

U.S. Pat. No. 5,886,037 discloses food compositions for treatment of various diseases which may be associated with the metabolic syndrome (syndrome X), including hyperlipoproteinaemia, obesity, hyperuricemia, hypertension, fatty liver, diabetes type II, insulin resistance and atherosclerotic vascular disease. The disclosed compositions contain medium-chain fatty acids and n-3 polyunsaturated long chain fatty acids.

U.S. Pat. No. 5,158,975 describes the use of stearidonic acid for prevention and treatment of inflammatory conditions, including allergic disorders, skin disorders, rheumatic disorders, and those following trauma, shock and pathologies. Stearidonic acid (SDA) and its metabolites, EPA and DHA, are said to inhibit biosynthesis of leukotrienes which are involved in the inflammation process.

U.S. Pat. No. 5,562,913 describes a method of treating n-6 or n-3 essential fatty acid deficits in smokers. The method involves administering to the smoker a formulation containing an n-6 essential fatty acid, an n-3 essential fatty acid, or a mixture of n-6 and n-3 fatty acids.

SUMMARY OF THE INVENTION

The present invention is directed towards a method for treating or preventing cancer in a mammal. The method involves administering to a mammal in need thereof a cancer inhibiting amount of stearidonic acid (18:4 n-3), eicosatetraenoic acid (20:4 n-3), docosapentaenoic acid (22:5 n-3) or mixtures thereof.

DETAILED DESCRIPTION OF THE INVENTION

As used herein, the term "treatment" includes partial or total inhibition of growth, spreading or metastasis of benign tumors, cancerous tumors and polyps, as well as partial or total destruction of tumor and polyp cells. The term "prevention" includes either preventing the onset of clinically evident tumors or polyps altogether or preventing the onset of a preclinically evident stage of tumor or polyp development in individuals at risk. The term "prevention" also includes prevention of initiation for malignant cells or to arrest or reverse the progression of premalignant cells to malignant cells. This includes those at risk for developing tumors and/or polyps.

The present inventors have discovered that administration of stearidonic acid (SDA; 18:4 n-3) to mammals raises the tissue levels of eicosapentaenoic acid (EPA) and docosahexaenoic acid (DHA) in the mammals to a higher level than does administration of an equivalent amount of α-linolenic acid (ALA; 18:3 n-3). In addition, the present inventors have discovered that SDA is converted to EPA and DHA at a rate and efficiency that permits the use of SDA as a precursor to EPA and DHA for treating or preventing cancer. The present inventors also have surprisingly discovered that dietary SDA may be more effective than even dietary EPA and DHA in inhibiting tumorigenesis of the large intestine.

Moreover, administering SDA to a patient rather than EPA and/or DHA takes advantages of "physiological channeling", in which the metabolism of SDA to EPA and DHA is ultimately controlled by the body's fatty acid metabolism, leading to optimal distribution in lipid pools affecting tumorigenesis (e.g., competing with arachidonic acid metabolism). This metabolic control may result in a more efficacious distribution of EPA and DHA than that provided by direct administration of EPA and/or DHA. Additionally, because SDA has a smaller chain length, and fewer unsaturated bonds than EPA and DHA, SDA may exhibit more desirable organoleptic properties than either EPA or DHA. Consequently, SDA may serve as an especially attractive substitute for EPA and DHA in a number of applications, including for example, functional foods or nutritional supplements.

Cancers which may be treated or prevented by the method of this invention include epithelial cell cancers, such as colon cancer, breast cancer, prostate cancer and lung cancer. Other cancers which may be treated or prevented by the method of this invention include brain cancer, bone cancer, adenocarcinoma, gastrointestinal cancers such as lip cancer, mouth cancer, esophageal cancer, small bowel cancer and stomach cancer, liver cancer, bladder cancer, pancreatic cancer, ovarian cancer, cervical cancer, renal cell carcinoma, and skin cancer such as squamous cell and basal cell cancers.

When administered to a mammal, SDA may be in any biologically active form. For example, SDA may be in the carboxylic acid form, or may instead be in the form of a lipid, a carboxylate salt, an ester, an amide or some other pharmacologically acceptable carboxylic acid derivative. Besides SDA, other metabolites of ALA which may be used in the present invention as precursors to EPA and DHA to treat or prevent cancer include eicosatetraenoic acid (20:4 n-3), docosapentaenoic acid (DPA n-3; 22:5n-3) and mixtures thereof.

The α-linolenic acid metabolites may be administered in the form of a pharmaceutical, nutritional or food preparation. Those of ordinary skill in the art of preparing pharmaceutical formulations can readily formulate pharmaceutical compositions having one or more metabolites of α-linolenic acid using known excipients (e.g., saline, glucose, starch, etc.). The pharmaceutical compositions may be formulated according to the desired method of administration. For example, pharmaceutical formulations containing one or more α-linolenic acid metabolites may be prepared for oral, enteral, parenteral or rectal administration.

Similarly, those of ordinary skill in the art of preparing nutritional formations (e.g., nutritional supplements) can readily formulate nutritional compositions having α-linolenic acid metabolites. And those of ordinary skill in the art of preparing food or food ingredient formulations can readily formulate food compositions or food ingredient compositions having α-linolenic acid metabolites.

The dosing regimen will depend upon the particular α-linolenic acid metabolite administered and the desired therapeutic or prophylactic effect. Typically, the amount of α-linolenic acid metabolite administered will be between about 1 mg/Kg/day and about 300 mg/Kg/day. Preferably, the amount of the metabolite administered is between about 10 mg/Kg/day and about 150 mg/Kg/day. The desired dosage may be administered as most efficacious, generally from 1–5 does per day, desirably from 1–3 doses per day.

Preferably, the α-linolenic acid metabolite administered to the mammal is SDA or a combination of SDA and at least one other ALA metabolite.

The examples which follow are intended to illustrate certain preferred embodiments of the invention, and no limitation of the invention is implied. The n-3 PUFAs used in all of the following examples were in the free acid form (100% pure) when used in cell culture and in the ethyl ester form (>85% pure) when administered in vivo. The ethyl esters of stearidonic acid (SDA-EE), eicosapentaenoic acid (EPA-EE) and docosahexaenoic acid (DHA-EE) were derived from fish oil, and were obtained from KD Pharma (Bexbach, Germany). The ethyl ester of stearidonic acid was further purified by Callanish, Ltd. (Scotland, U.K.) to increase the SDA-EE content from approximately 60% to 85% and also to decrease the EPA-EE content from approximately 8% to 0.2%. The ethyl esters of α-linolenic acid (ALA-EE) and γ-linolenic acid (GLA-EE), which were derived from plant oils, were at least 95% pure and were purchased from Callanish, Ltd. Administration of the fatty acid ethyl esters in rodents was scaled allometrically by caloric equivalency to reflect the human equivalent amount of fatty acid consumed per day (=g/day human equivalent dose).

EXAMPLE 1

The US17 Diet

In order to study the effects of PUFAs on colon tumor formation and promotion in rodents, a diet (the "US17 diet") was designed to mimic the human western diet. The human western diet contains high levels of saturated fatty acids and linoleic acid, both of which have been linked to cancer formation. The components of the US17 diet are set forth in Tables 1–6, below.

TABLE 1

Ingredients of the US17 diet.

| Ingredient | Amount (grams) |
|---|---|
| Casein, Alcx | 200 |
| L-Cystine | 3 |
| Corn Starch | 240 |
| Maltodextrin 10 | 75 |
| Sucrose | 100 |
| Cellulose | 50 |
| Cocoa Butter (Deodorized) | 37.5 |
| Linseed Oil | 4.5 |
| Palm Oil (Bleached, deodorized) | 52.5 |
| Safflower Oil, USP | 28.5 |
| Sunflower Oil, Trisun Extra | 27 |
| t-BHQ | 0.03 |
| Salts (See Table 2) | 10 |
| Dicalcium Phosphate | 13 |

TABLE 1-continued

Ingredients of the US17 diet.

| Ingredient | Amount (grams) |
|---|---|
| Calcium carbonate | 5.5 |
| Potassium citrate (Monohydrate) | 16.5 |
| Vitamins (See Table 3) | 10 |
| Choline bitartrate | 2 |
| α-Vitamin E acetate (500 IU/gm) | 0.13 |
| Total (grams) | 875.16 |

TABLE 2

Salt mixture of the US17 diet

| Ingredient | Amount (gm) |
|---|---|
| Sodium Chloride | 25.90 |
| Magnesium Oxide | 4.19 |
| Magnesium Sulfate.7$H_2$O | 25.76 |
| Chromium Potassium Sulfate.12$H_2$O | 0.19 |
| Cupric Carbonate | 0.10 |
| Sodium Fluoride | 0.02 |
| Potassium Iodate | 0.003 |
| Ferric Citrate | 2.10 |
| Manganous Carbonate | 1.23 |
| Ammonium Molybdate.4$H_2$O | 0.03 |
| Sodium Selenite | 0.003 |
| Zinc Carbonate | 0.56 |
| Sucrose | 39.91 |
| Total | 100 |

TABLE 3

Vitamin mixture of the US17 diet

| Ingredient | Amount (gm) |
|---|---|
| Vitamin A Palmitate 500,00 IU/gm | 0.08 |
| Vitamin D3 100,00 IU/gm | 0.10 |
| Vitamin E Acetate 500 IU/gm | 1.00 |
| Menadione Sodium Bisulfite | 0.008 |
| Biotin 1.0% | 0.20 |
| Cyanocobalamin 0.1% | 0.10 |
| Folic Acid | 0.02 |
| Nicotinic Acid | 0.30 |
| Calcium Pantothenate | 0.16 |
| Pyridoxine-HCl | 0.07 |
| Riboflavin | 0.06 |
| Thiamin HCl | 0.06 |
| Sucrose | 97.84 |
| Total | 100 |

TABLE 4

Fatty acid content of the US17 diet

| Fatty Acid | Amount | |
|---|---|---|
| C14, Myristic | 0.7 | gms |
| C16, Palmitic | 34.6 | gms |
| C16:1, Palmitoleic | 0.2 | gms |
| C18, Stearic | 17.5 | gms |
| C18:1, Oleic | 60.5 | gms |
| C18:2, Linoleic | 30.2 | gms |
| C18:3, Linolenic | 3.1 | gms |
| C20, Arachidic | 0.4 | gms |
| Saturated | 36.1 | weight % |

TABLE 4-continued

Fatty acid content of the US17 diet

| Fatty Acid | Amount |
| --- | --- |
| Monounsaturated | 41.3 weight % |
| Polyunsaturated | 22.6 weight % |

TABLE 5

Nutritional content of the US17 diet

| Nutrient | Amount |
| --- | --- |
| Protein | 22.7 weight % |
| Carbohydrate | 48.6 weight % |
| Fat | 17.1 weight % |
| Fiber | 5.7 weight % |
| Protein | 20.7 kcal % |
| Carbohydrate | 44.2 kcal % |
| Fat | 35.1 kcal % |

TABLE 6

Comparison between rodent US17 diet and human, western diet

| | Kcal % | |
| --- | --- | --- |
| Nutrient | Rodent diet (US17) | Human Diet |
| Protein | 21 | 15 |
| Carbohydrate | 44 | 50 |
| Fat | 35 | 35 |
| Fatty Acid Composition | | |
| <C16 | 0.2 | 1.6 |
| 16:0 | 8.6 | 7.9 |
| 18:0 | 4.3 | 3.9 |
| 18:1 n-9 (oleic acid cassette) | 14.6 | 14.0 |
| 18:2 n-6 | 7.0 | 6.9 |
| 18:3 n-3 | 0.7 | 0.7 |
| n-6:n-3 ratio | 10:1 | 10:1 |

The fatty acid test agent was substituted for oleic acid (=oleic acid cassette) and the dose, when scaled allometrically, was in the range readily consumed by humans (i.e., 0.1 to 10 g/day).

EXAMPLE 2

Uptake of $^{14}$C-Ala, $^{14}$C-SDA and $^{14}$C-EPA by HepG2 Cells

The uptake of stearidonic acid by HepG2 cells was compared to that of α-linolenic acid and eicosapentaenoic acid.

To a culture medium containing HepG2 cells was added 20 μM $^{14}$C-ALA, $^{14}$C-SDA or $^{14}$C-EPA complexed to fatty acid free BSA. The amount of $^{14}$C-ALA, $^{14}$C-SDA or $^{14}$-EPA EPA Taken up by the HepG2 cells was measured 6 hours, 24 hours and 48 hours after addition of the fatty acid. A scintillation counter was used to measure the total amount of radioactivity in the HepG2 cells and the amount remaining in the medium.

Figure 1:
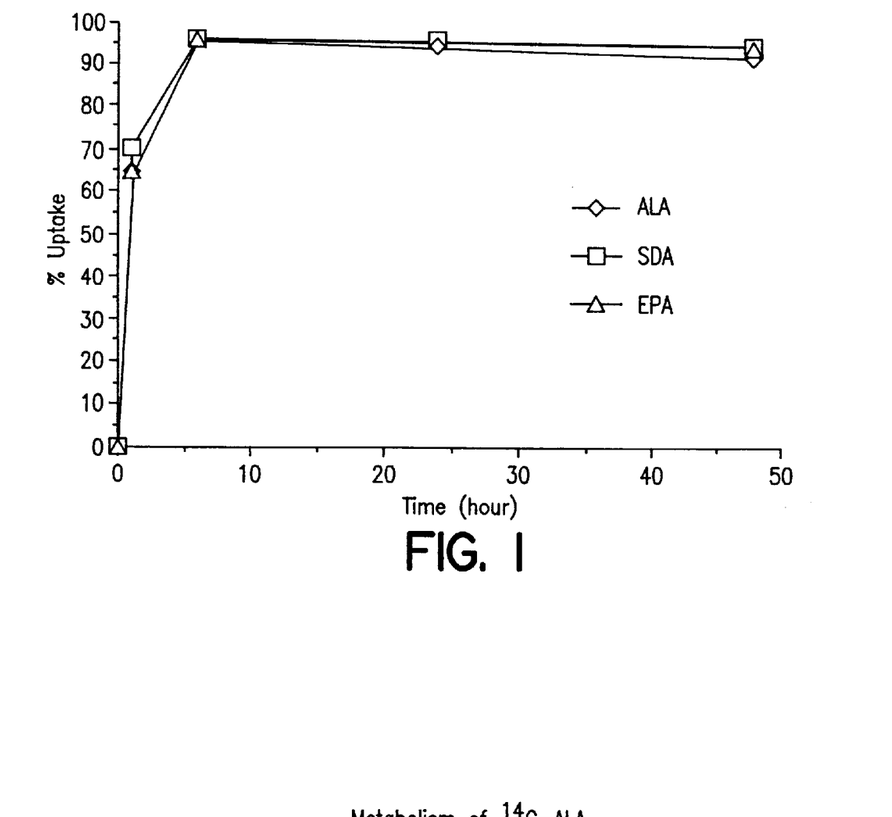
FIG. 1 illustrates the rate of uptake of radiolabeled ALA, SDA and EPA in HepG2 cells.

The results of these measurements are shown in FIG. 1. As can be seen in FIG. 1, $^{14}$C-ALA, $^{14}$C-SDA and $^{14}$C-EPA were taken up equally by HepG2 cells. Approximately 95% of each radiolabeled fatty acid was taken up by the cells within the first six hours of incubation.

EXAMPLE 3

Metabolism of Stearidonic Acid to Long Chain n-3 Polyunsaturated Fatty Acids in HepG2 Cells The metabolism of stearidonic acid to long chain n-3 PUFAs (eicosatetraenoic acid (20:4n-3), eicosapentaenoic acid (20:5n-3), docosapentaenoic acid (22:5n-3), and docosahexaenoic acid (22:6n-3)) in HepG2 cells was compared to that of α-linolenic acid.

HepG2 cells were allowed to take up $^{14}$C-ALA or $^{14}$C-SDA as described in Example 2. The total amount of $^{14}$C-EPA, $^{14}$C-DPA and $^{14}$C-DHA present in the HepG2 cells was measured 6 hours, 24 hours and 48 hours after addition of the fatty acid by argentation thin layer chromatography (TLC). The amount of each fatty acid present as a band on the TLC plate was quantified by electronic autoradiography using an Instant Imager supplied by Packard (Meriden, Conn.).

Figure 2:
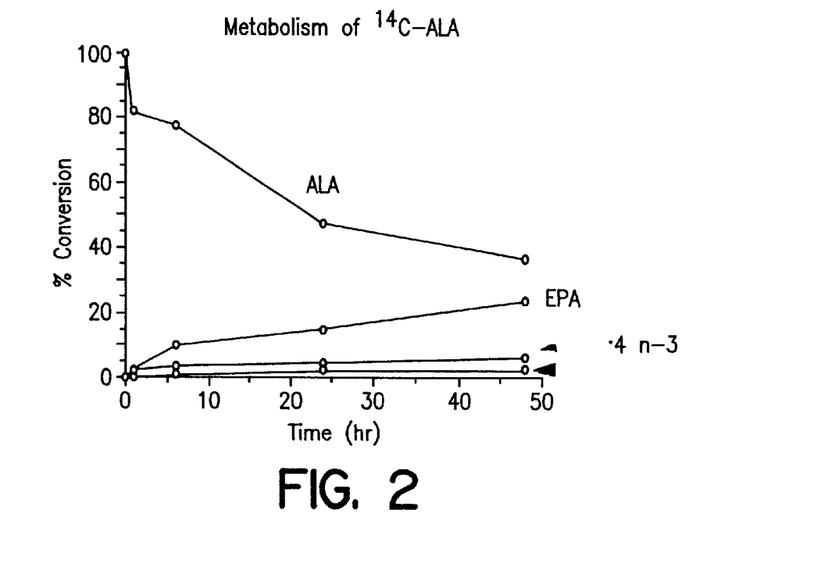
FIG. 2 illustrates the rate of metabolism of radiolabeled ALA to long chain n-3 polyunsaturated fatty acid metabolites in HepG2 cells.
Figure 3:
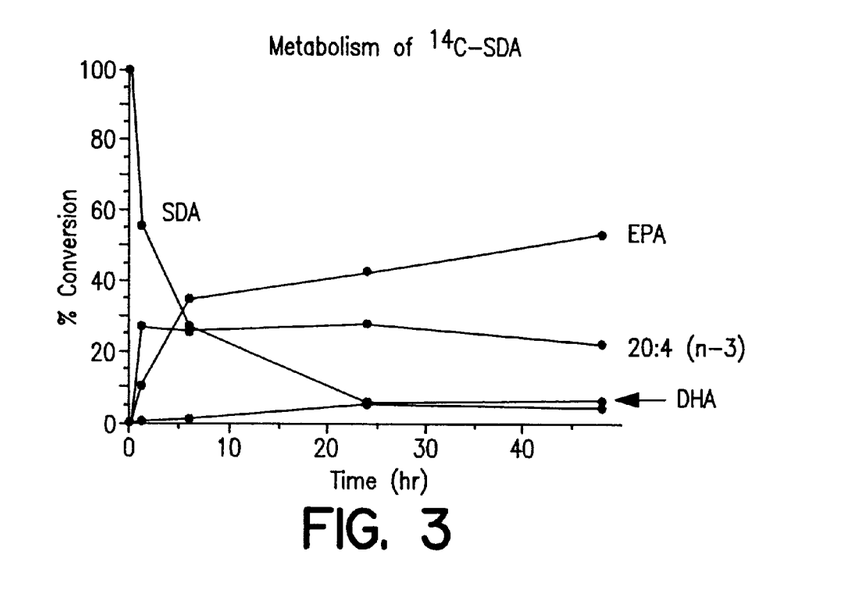
FIG. 3 illustrates the rate of metabolism of radiolabeled SDA to long n-3 chain polyunsaturated fatty acid metabolites in HepG2 cells.

The results of these measurements are shown in FIGS. 2 and 3. FIG. 2 shows the metabolism of ALA to long chain n-3 PUFAs. FIG. 3 shows the metabolism of SDA to long chain n-3 PUFAs. A comparison of FIG. 2 to FIG. 3 shows that the metabolism of SDA in Hep2G cells to long chain n-3 PUFAs is faster than that of ALA. Nearly 95% of the $^{14}$C-SDA was metabolized to $^{14}$C-fatty acid end products (i.e., EPA or DHA) or $^{14}$C fatty acid intermediates (i.e., 20:4 n-3, 22:5 n-3 and 24:5 n-3). $^{14}$C-SDA was metabolized more efficiently to $^{14}$C-EPA than was $^{14}$C-ALA (55% versus 24%).

EXAMPLE 4

Metabolism of Stearidonic Acid to EPA and DHA in HepG2 Cells

The metabolism of stearidonic acid to eicosapentaenoic acid (20:5 n-3) and docosahexaenoic acid (22:6 n-3)) in HepG2 cells was compared to that of α-linolenic acid.

HepG2 cells were allowed to take up $^{14}$C-ALA, $^{14}$C-SDA or $^{14}$C-EPA as described in Example 2. The amount of $^{14}$C-EPA and $^{14}$C-DHA present in the HepG2 cells was measured 6 hours, 24 hours and 48 hours after addition of the fatty acids by argentation thin layer chromatography (TLC) as described in Example 3. The amount of $^{14}$C-EPA and $^{14}$C-DHA present as bands on the TLC plate were quantified by electronic autoradiography using an Instant Imager as described in Example 3.

Figure 4:
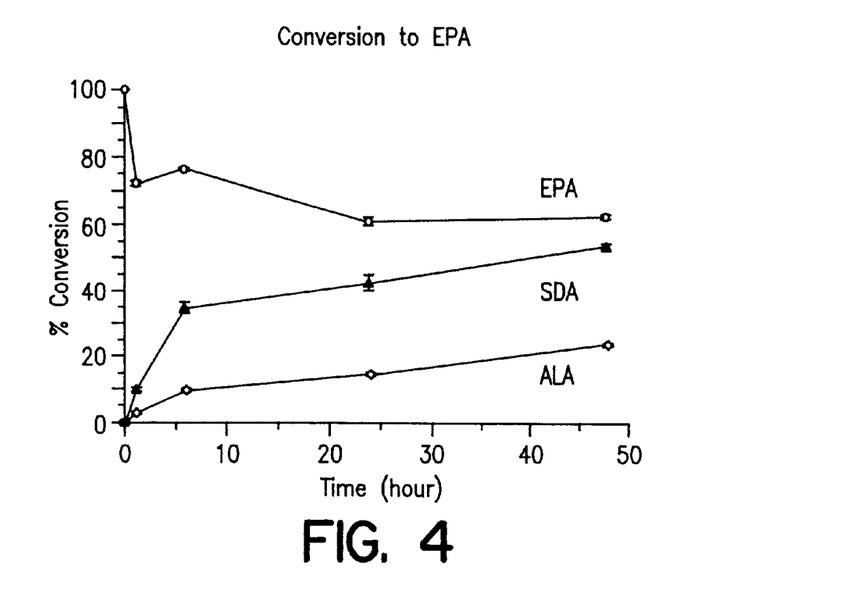
FIG. 4 illustrates the rate of metabolism of radiolabeled ALA and SDA to EPA in HepG2 cells.
Figure 5:
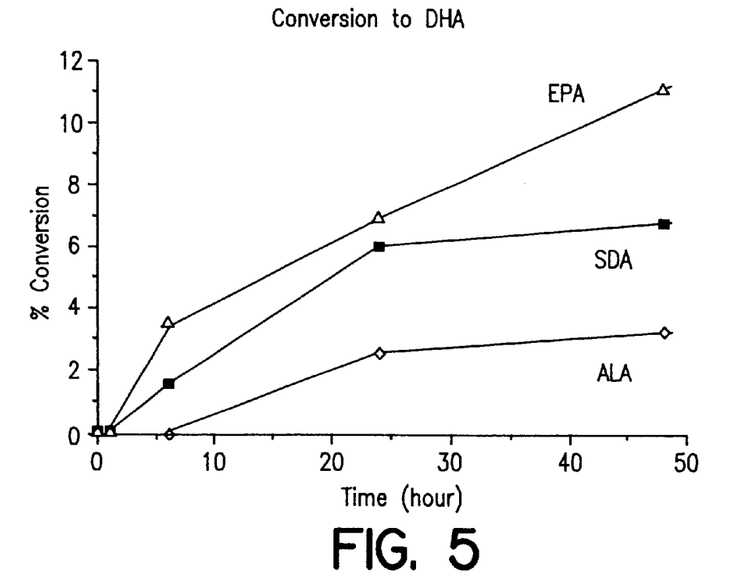
FIG. 5 illustrates the rate of metabolism of radiolabeled ALA, SDA and EPA to DHA in HepG2 cells.

The results of these measurements are shown in FIGS. 4 and 5. FIG. 4 shows the metabolism of radiolabeled ALA and SDA to EPA. Radiolabeled EPA was included as a control to evaluate its maintenance in HepG2 cells over time. FIG. 5 shows the metabolism of radiolabeled ALA, SDA and EPA to DHA. FIG. 4 shows that SDA was metabolized more efficiently to EPA than was ALA (55% versus 24%). The amount of EPA derived from SDA was actually quite similar to the amount of EPA that remained after incubation with EPA itself (55% versus 63%). FIG. 5 shows that SDA was metabolized to DHA more efficiently than was ALA (6% versus 3%). In comparison, approximately 11% of EPA was metabolized to DHA. Overall, the results showed that SDA was metabolized to EPA and further to DHA at a rate that was approximately twice that of ALA.

EXAMPLE 5

Metabolism of Stearidonic Acid in Mice (Time Course Analysis Using Radiolabeled Fatty Acids)

The metabolism of stearidonic acid to long chain n-3 polyunsaturated fatty acids (i.e., eicosapentaenoic acid (EPA), docosapentaenoic acid (DPA n-3), and docosahexaenoic acid (DHA)) in mouse liver was compared to that of α-linolenic acid, eicosapentaenoic acid and docosahexaenoic acid. The method used was a time course study using $^{14}$C-labeled fatty acids.

Figure 6:
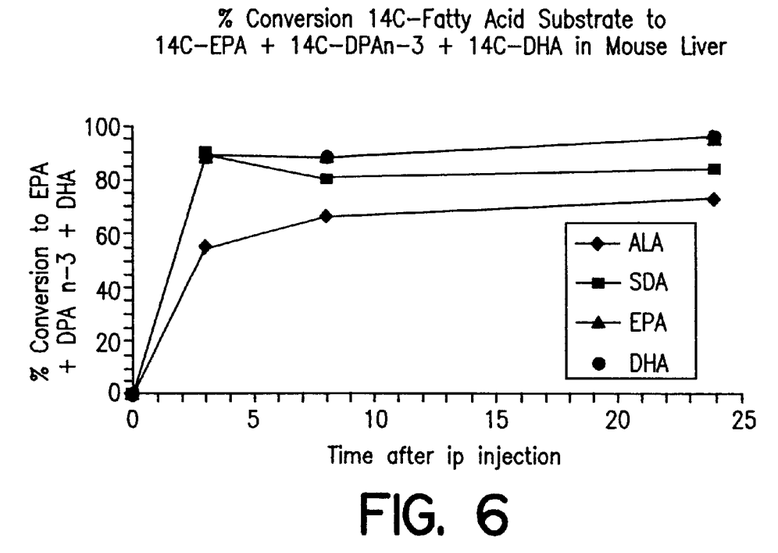
FIG. 6 illustrates the conversion of radiolabeled ALA, SDA and EPA to long chain n-3 polyunsaturated fatty acid metabolites in mouse liver.
Figure 7:
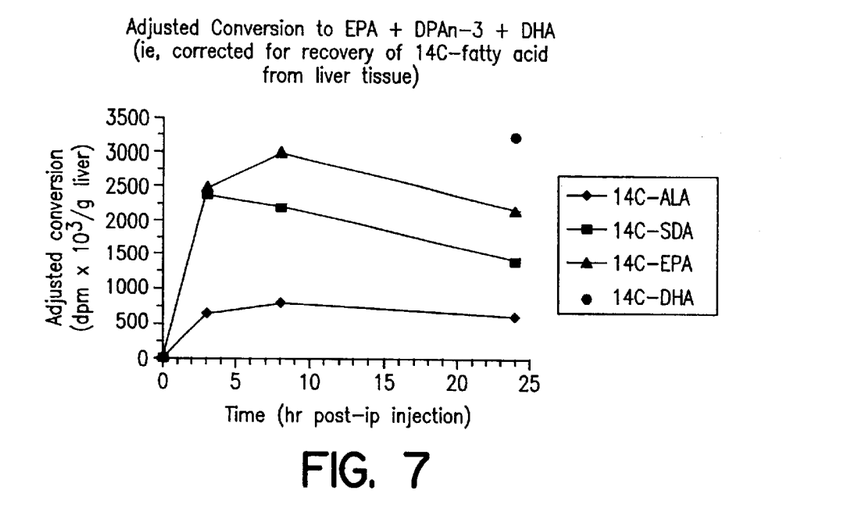
FIG. 7 illustrates the conversion of radiolabeled ALA, SDA and EPA to long chain n-3 polyunsaturated fatty acid metabolites in mouse liver, corrected for recovery of radiolabeled fatty acid from liver tissue.

Mice were fed the US17 diet for a period of one month in order to achieve steady-state fatty acid metabolism. After achieving steady-state fatty acid metabolism, the mice were administered an intraperitoneal injection containing 10 μCi of $^{14}$C-ALA, $^{14}$C-SDA, $^{14}$C-EPA OR $^{14}$C-DHA. Mice were sacrificed 3 hours, 8 hours or 24 hours post-injection, and the total amount of $^{14}$C-EPA, $^{14}$C-DPA n-3 and $^{14}$C-DHA was measured by argentation thin layer chromatography followed by direct electronic autoradiography, as described in Example 3. The results of these experiments are shown in FIG. 6. FIG. 6 shows the order of metabolism of the PUFAs to be DHA=EPA>SDA>ALA at 24 hours. This difference in metabolism rates was especially magnified when the conversion to EPA+DPA+DHA was adjusted to $^{14}$C counts recovered from liver tissue. With ALA, the recovery was notably lower, most probably due to the propensity of ALA to undergo beta-oxidation. This adjustment is shown in FIG. 7, which further shows that SDA is metabolized to long chain n-3 PUFAs more efficiently than ALA in vivo.

EXAMPLE 6

Metabolism of Stearidonic Acid in Mice (End Point Analysis Using Cold Fatty Acid Ethyl Esters)

The metabolism of n-6 and n-3 PUFAs in rats and mice is similar to that of humans. Lands, W. E. M., Morris, A., Libelt, B., Lipids, Vol. 25(9), pp. 505–516 (1990). As such, fatty acid metabolic results from studies with rats and mice would be predicted to be similar in humans.

The metabolism of stearidonic acid to long chain n-3 polyunsaturated fatty acids (i.e., eicosapentaenoic acid (EPA), docosapentaenoic acid (DPA n-3) and docosahexaenoic acid (DHA)) in mouse liver was compared to that of α-linolenic acid, eicosapentaenoic acid and docosahexaenoic acid. The method used was a non-radioactive, dose response, metabolic end-point study.

Mice were fed a US17 diet containing α-linolenic acid ethyl ester (ALA-EE), stearidonic acid ethyl ester (SDA-EE), eicosapentaenoic acid ethyl ester (EPA-EE), or docosahexaenoic acid ethyl ester (DHA-EE) in an amount equivalent to a human western diet containing 1, 3 or 10 g/day of the fatty acid (g/day human equivalent dose). In order to maintain a 17% fat (37 en %) content in the US17 diet, oleic acid (18:1 n-9), as an oleic acid cassette, was removed from the US17 diet in an amount equal to the amount of fatty acid ester that was added. Oleic acid was selected as the replacement fatty acid because literature reports indicate that oleic acid is neutral with respect to inflammation and cancer.

After one month on the respective US17-based diets, the mice were sacrificed and the fatty acid composition of each of their livers was analyzed by gas chromatography. The results of these analyses are pressured in FIG. 8.

Figure 8:
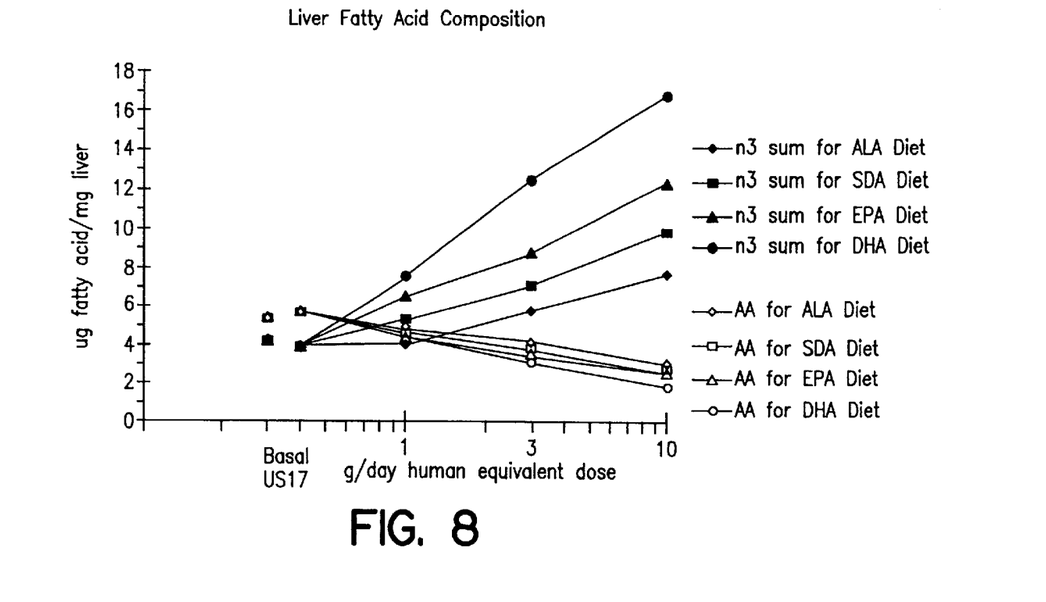
FIG. 8 illustrates the total amount of long chain n-3 polyunsaturated fatty acids accumulated in mouse liver upon being fed the US17 diet containing increasing amounts of ALA, SDA, EPA or DHA in the ethyl ester form.

FIG. 8 shows that the sum of the long chain n-3 PUFAs (i.e., EPA+DPA n-3+DHA) increased dose dependently in liver tissue in the following rank order: DHA-EE>EPA-EE>SDA-EE>ALA-EE. These results showed that SDA was metabolized to long chain n-3 polyunsaturated fatty acids better than ALA. FIG. 8 also shows that each of the dietary n-3 PUFAs decreased the level of arachidonic acid in liver tissue dose dependently. This is significant because arachidonic acid metabolites (e.g., prostaglandins, leukotrienes, and HETEs (hydroxyeicosatetraenoic acid)) are correlated with tumorigenesis. The group "basal" refers to mice that were fed the standard rodent chow diet just prior to switching to diets that were US17 based. The results showed that the level of the sum of the long chain n-3 PUFAs or arachidonic acid was the same, indicating that the US17 diet did not significantly alter fatty acid composition compared to the standard rodent chow diet.

EXAMPLE 7

Metabolism of Stearidonic Acid in Rats (End Point Analysis Using Cold Fatty Acid Ethyl Esters)

The metabolism of stearidonic acid to long chain n-3 polyunsaturated fatty acids (i.e., eicosapentaenoic acid (EPA), docosapentaenoic acid (PIA n-3) and docosahexaenoic acid (DHA)) in rat liver was compared to that of α-linolenic acid, eicosapentaenoic acid and docosahexaenoic acid. The method used was as described in Example 6 except that rats were used in place of mice. The results of these analyses are presented in FIG. 9.

Figure 9:
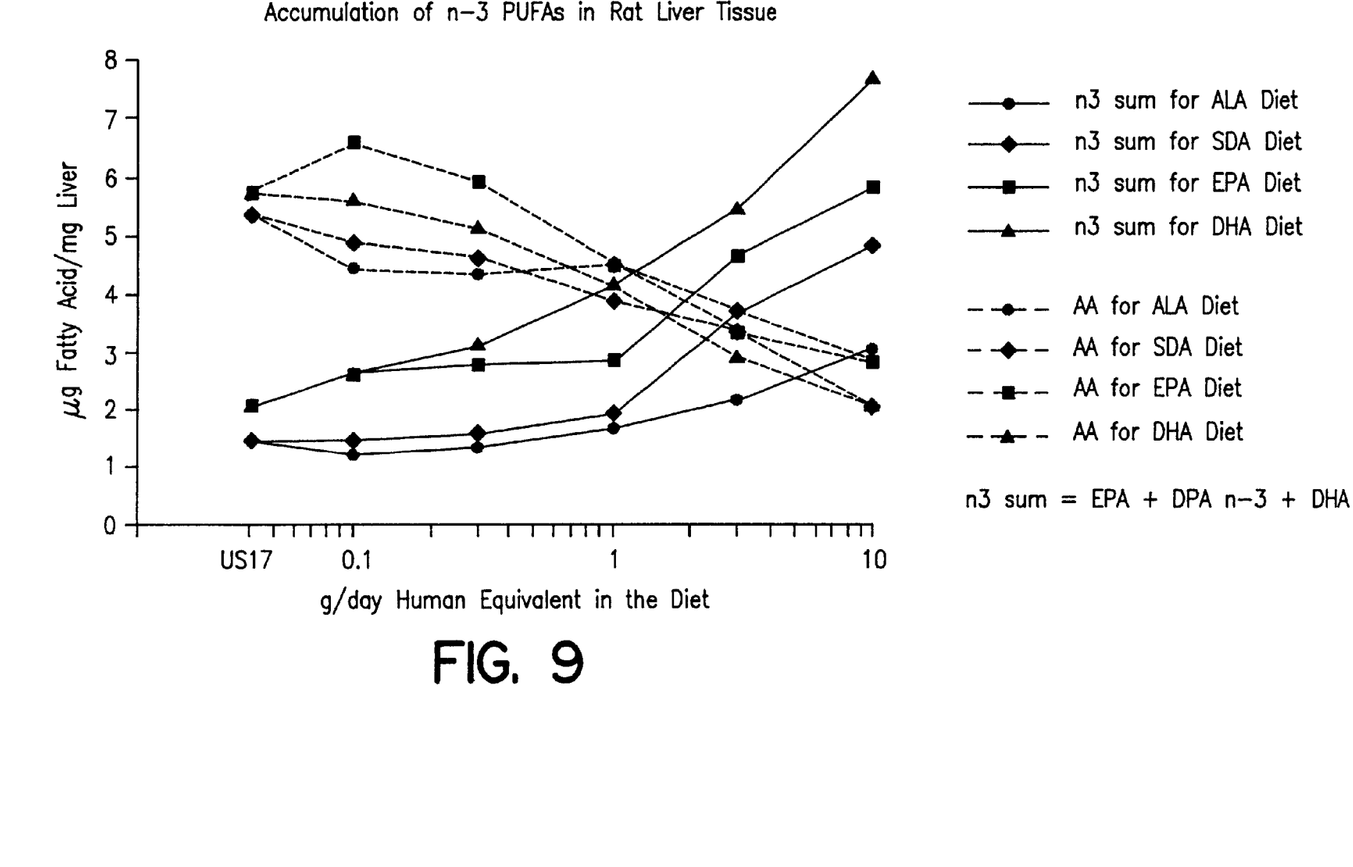
FIG. 9 illustrates the total amount of long chain n-3 polyunsaturated fatty acids accumulated in rat liver upon being fed the US17 diet containing increasing amounts of ALA, SDA, EPA or DHA in the ethyl ester form.

FIG. 9 shows that the sum of the long chain n-3 PUFAs (i.e., EPA+DPA n-3, and DHA) accumulated dose dependently in liver tissue in the following rank order: DHA-EE>EPA-EE>SDA-EE>ALA-EE. These results showed that SDA was metabolized to long chain n3 polyunsaturated fatty acids better than ALA. FIG. 9 also shows that each of the dietary n-3 PUFAs decreased the level of arachidonic acid in liver tissue dose-dependently. SDA caused a greater decrease in the level of arachidonic acid than did either ALA or EPA.

EXAMPLE 8

Effect of n-3 and n-6 PUFAs on Intestinal Cancer in the Min/+ Mouse Model

The efficacy of select n-3 and n-6 polyunsaturated fatty acids was evaluated in the Min/+ mouse model of intestinal cancer. The following fatty acid ethyl esters were tested for their effect on intestinal polyp formation: 1) ALA-EE; 2) SDA-EE; 2) EPA-EE; 4) DHA-EE; 5) GLA-EE (α-linolenic adid, 18:3 n-6); and 6) CLA-EE (conjugated linoleic acid; c9t11-18:2 (77%)+c9c11-18:2 (18%)+other isomers (5%)).

These fatty acid ethyl esters were added to the US17 diet to provide 10 g/day human equivalent dose (3% wt.). The NSAID, sulindac (320 ppm), served as the positive control. In order to maintain a 17% fat (37 en%) content in the US17 diet, oleic acid (18:1 n-9) was removed from the US17 diet in an amount equal to the amount of the fatty acid ethyl ester that was added. Mice were received at approximately five weeks of age and were fed the test diets upon receipt. After seven weeks on the respective test diet, the mice were sacrificed and the intestinal polyps were counted and measured. The results of these analyses are presented in Table 6.

TABLE 6

Effect of various fatty acids on tumor size and number in the large and small intestine of Min/+ mice

| | US17 (n = 10) | ALA (n = 10) | CLA (n = 9) | DHA (n = 10) | EPA (n = 10) | GLA (n = 9) | SDA (n = 10) | Sulindac (n = 9) |
|---|---|---|---|---|---|---|---|---|
| Total large intestine tumors/group | 13 (7/10) | 8 (5/10) | 10 (5/9) | 18 (9/10) | 9 (6/10) | 11 (6/9) | 2 (2/10) | 2 (2/9) |
| Avg. large intestine tumors/mouse | $1.3 \pm 0.6^{ab}$ | $0.8 \pm 0.3^{bcd}$ | $1.1 \pm 0.4^{abcd}$ | $1.8 \pm 0.4^{a}$ | $0.9 \pm 0.3^{abcd}$ | $1.2 \pm 0.4^{abc}$ | $0.2 \pm 0.1^{d}$ | $0.2 \pm 0.2^{cd}$ |
| Avg. large intestine tumor size | $2.96 \pm 0.20^{b}$ | $2.75 \pm 0.46^{ab}$ | $3.03 \pm 0.52^{a}$ | $3.01 \pm 0.20^{a}$ | $2.48 \pm 0.39^{ab}$ | $2.57 \pm 0.30^{ab}$ | $1.50 \pm 0.00^{b}$ | $2.00 \pm 0.00^{ab}$ |
| Avg. large intestine tumor load | $3.70 \pm 1.51^{ab}$ | $2.15 \pm 0.83^{bcd}$ | $3.47 \pm 1.29^{ab}$ | $5.06 \pm 0.85^{a}$ | $2.25 \pm 0.75^{bcd}$ | $3.25 \pm 1.34^{abc}$ | $0.30 \pm 0.20^{d}$ | $0.44 \pm 0.29^{cd}$ |
| Total small intestine tumors/group | 337 | 364 | 409 | 280 | 176 | 421 | 185 | 29 |
| Avg. small intestine tumors/mouse | $33.7 \pm 4.5^{ab}$ | $36.4 \pm 6.3^{ab}$ | $45.4 \pm 8.2^{a}$ | $28.0 \pm 5.6^{bc}$ | $17.6 \pm 2.2^{cd}$ | $46.8 \pm 7.1^{a}$ | $18.5 \pm 1.9^{c}$ | $3.2 \pm 1.1^{d}$ |
| Avg. small intestine tumor size (mm) | $1.32 \pm 0.05^{a}$ | $1.23 \pm 0.04^{ab}$ | $1.24 \pm 0.03^{ab}$ | $1.16 \pm 0.04^{ab}$ | $1.05 \pm 0.03^{b}$ | $1.30 \pm 0.04^{ab}$ | $1.07 \pm 0.02^{ab}$ | $1.25 \pm 0.29^{ab}$ |
| Avg. small intestine tumor load | $43.62 \pm 5.3^{ab}$ | $45.67 \pm 8.66^{ab}$ | $57.84 \pm 11.70^{a}$ | $33.15 \pm 8.09^{bc}$ | $1834 \pm 2.04^{cd}$ | $61.62 \pm 10.36^{a}$ | $19.90 \pm 2.11^{cd}$ | $3.64 \pm 1.12^{d}$ |
| Total Avg. tumors/mouse | $35.0 \pm 4.5^{ab}$ | $37.2 \pm 6.6^{ab}$ | $46.6 \pm 8.3^{a}$ | $29.8 \pm 5.9^{bc}$ | $18.5 \pm 2.2^{a}$ | $48.0 \pm 7.4^{a}$ | $18.7 \pm 1.9^{a}$ | $3.4 \pm 1.2^{d}$ |
| Total Avg. overall tumor size (mm) | $1.32 \pm 0.04^{a}$ | $1.21 \pm 0.03^{bc}$ | $1.28 \pm 0.04^{ab}$ | $1.20 \pm 0.04^{bc}$ | $1.11 \pm 0.04^{cd}$ | $1.33 \pm 0.04^{a}$ | $1.08 \pm 0.02^{d}$ | $1.04 \pm 0.08^{d}$ |
| Total Avg. overall tumor load | $45.91 \pm 5.74^{ab}$ | $45.97 \pm 8.88^{ab}$ | $61.30 \pm 12.41^{a}$ | $35.60 \pm 7.10^{bc}$ | $20.28 \pm 2.23^{cd}$ | $64.84 \pm 11.05^{a}$ | $20.19 \pm 2.24^{cd}$ | $3.64 \pm 1.27^{d}$ |

Values are expressed as mean ± SEM.
Different superscripts indicate values in each row that are significantly different at p < 0.05.
Fisher's least significant difference multiple comparison method was used to determine differences amoung groups.
Each animal is given equal weight in determining average small intestine tumor size and overall tumor size.
Average colon tumor size is calculated only with animals bearing colonic tumors.
Tumor load = tumor number × tumor size and is expressed in mm.

As shown in Table 6, the analyses demonstrated that SDA was effective in decreasing polyp number (47%), polyp size (18%) and polyp load (number×size) (56%) in the large intestine and small intestine. It should be noted that while the terms polyp and tumor are used interchangeably, technically speaking, the lesions are polyps (i.e., early stage tumors or neoplasms).

Figure 10:
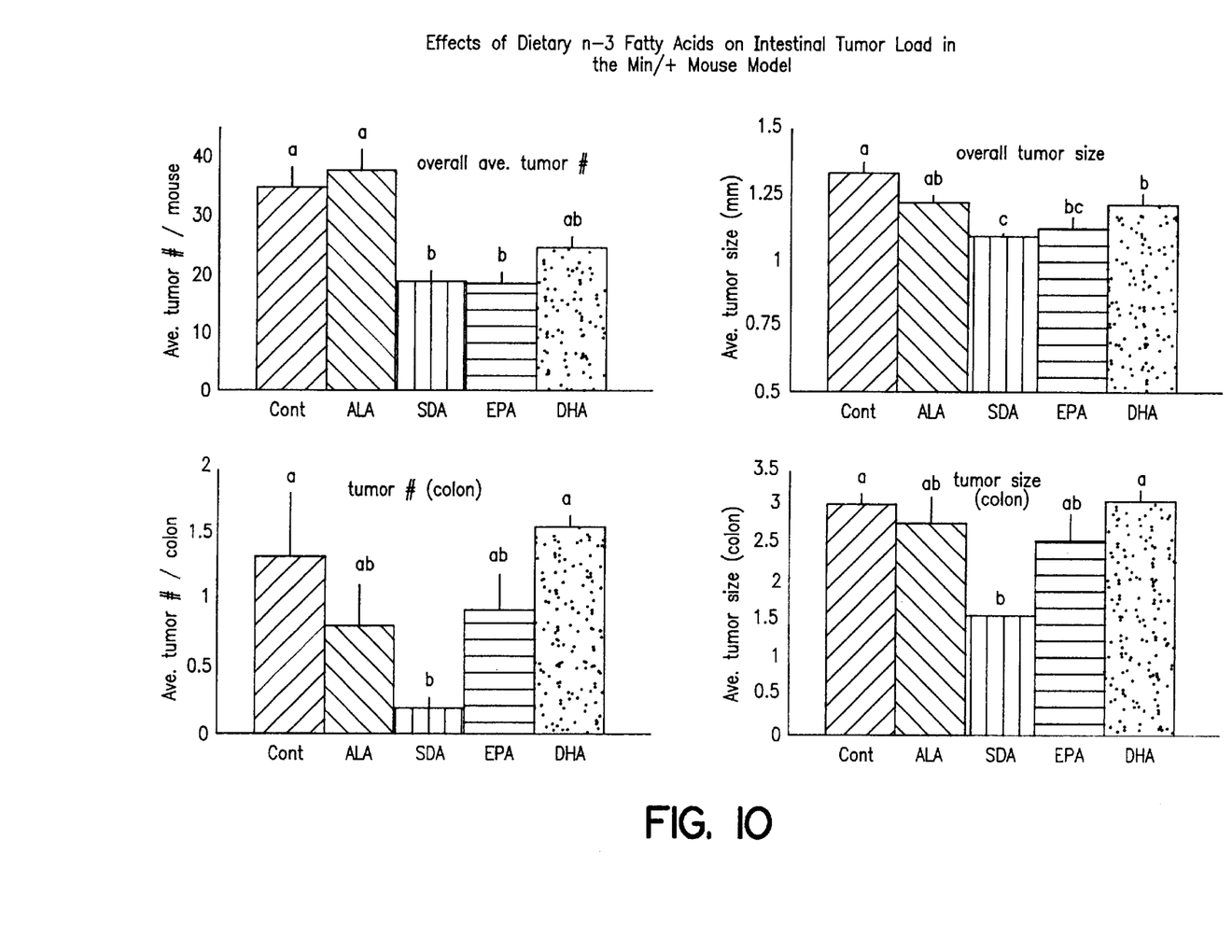
FIG. 10 illustrates the effects of ALA, SDA, EPA and DHA fed as ethyl esters on intestinal polyp number and size in the Min/+ mouse model of intestinal cancer.

Unexpectedly, the effectiveness of SDA in inhibiting polyp formation and development in the large intestine was comparable to that of sulindac, a NSAID commonly used as a positive control, and was greater than that of not only ALA, but also EPA and DHA. ALA and EPA were marginally efficacious, while DHA showed no efficacy in the large intestine. Likewise, unexpectedly the effectiveness of SDA in inhibiting polyp formation and development in the small intestine was comparable to that of EPA, and was greater than that of ALA and DHA. This is also shown in bar-graph form in FIG. 10. GLA and CLA, in contrast to SDA, EPA and DHA, appeared to increase polyp number; however, the differences were not significant relative to the US17 control.

EXAMPLE 9

Effect of n-3 and n-6 PUFAs on Tissue Levels of Arachidonic Acid in the Small Intestine The efficacy of select n-3 and n-6 polyunsaturated fatty acids in reducing the level of arachidonic acid in small intestine tissue was evaluated using the Min/+ mouse model. The following fatty acid ethyl esters were tested for their effect on intestinal fatty acid composition: 1) ALA-EE; 2) SDA-EE; 3) EPA-EE; 4) DHA-EE; 5) GLA-EE; and 6) CLA-EE. Fatty acid composition was determined in the small intestine because that is where the vast majority of polyps form.

Figure 11:
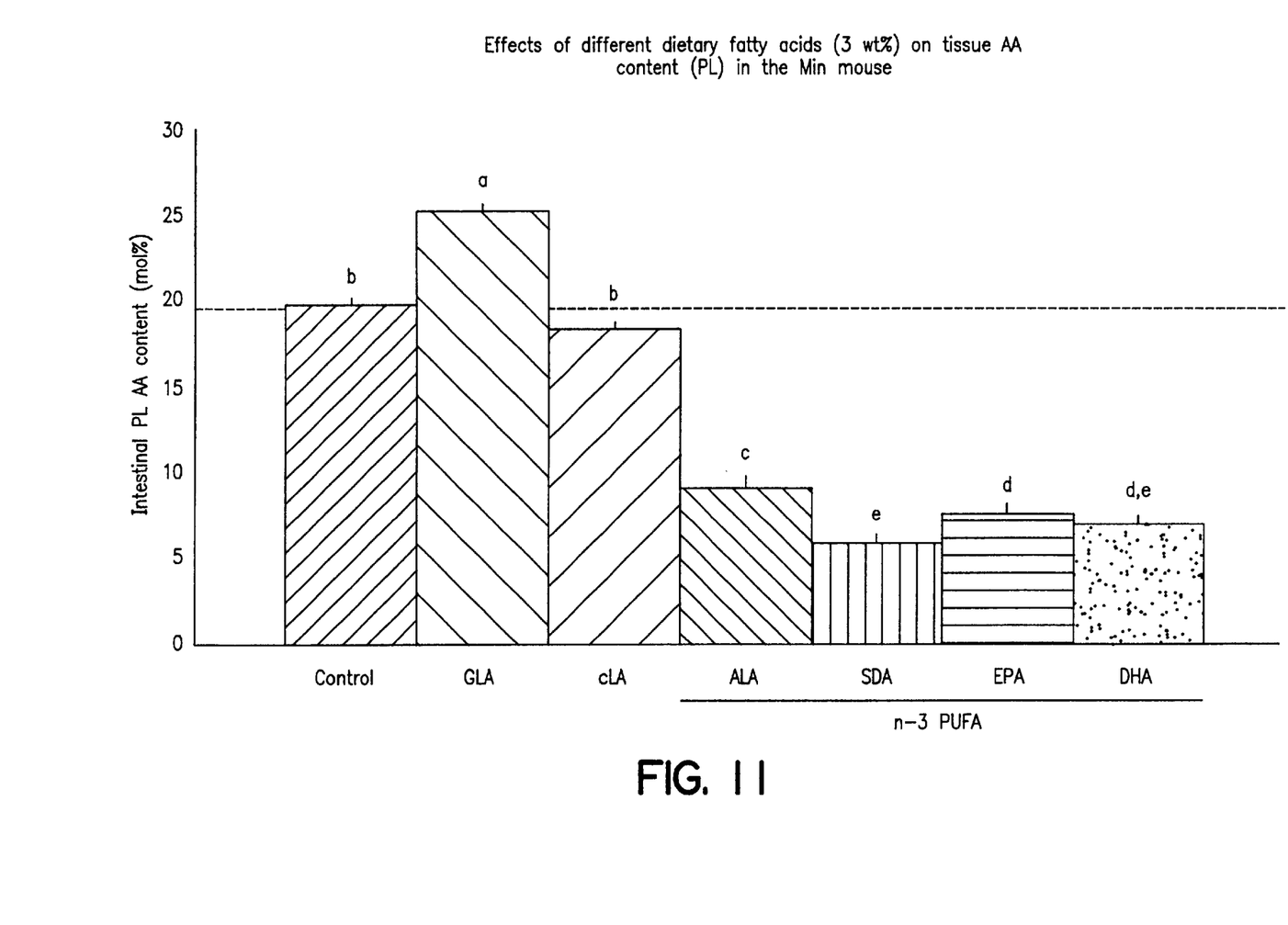
FIG. 11 illustrates the effects of ALA, SDA, EPA and DHA fed as ethyl esters on arachidonic acid content in the phospholipid (PL) fraction of mouse small intestine.

These fatty acid esters were added to the US17 diet as discussed in Example 8. The arachidonic acid level in the phospholipid fraction of the small intestines of the mice was determined by gas chromatography. The results of this analysis are presented in FIG. 11. In FIG. 11, bars labeled with the same letter (e.g., control and CLA, both labeled with a "b") have values which, statistically, are not different.

FIG. 11 shows that SDA was more effective than ALA, EPA and DHA in decreasing the level of arachidonic acid in the small intestine of the mice. Decreasing the level of arachidonic acid in tissues is desirable because arachidonic acid metabolites have been implicated in tumorigenesis (e.g., prostaglandins, leukotrienes, and HETEs).

EXAMPLE 10

Effect of Stearidonic Acid on Primary Tumor Growth in the Nude Mouse/HT-29 Cancer Model The efficacy of stearidonic acid (18:4n-3) in inhibiting primary tumor growth was evaluated using the nude mouse/

HT-29 model. The nude mouse/HT-29 model has been described previously. Hernandez-Alcoceloa R., Fernandez, F., Lacal, J C, Cancer Res., 59(13), 312-18 (1999); Fantini, J., Cancer J., 5(2) (1992).

Nude (i.e., immunodeficient) mice were fed the US17 diet for three weeks. HT-29 cells were cultured in RPMI-1640 medium supplemented with fetal bovine serum, penicillin, and streptomycin (Gibco, Grand Island, N.Y.) and maintained in a $CO_2$ atmosphere at 37° C. After achieving the optimal cell density, the HT-29 cells were rinsed and then suspended in phosphate buffered saline (PBS). A cell suspension was made in MATRIGEL (Becton Dickinson Labware, Bedford, Mass.). The suspension was ⅔ by volume cells in PBS and ⅓ by volume MATRIGEL. MATRIGEL provides an extracellular matrix secreted by endothelial cells. The matrix contains angiogenic and cell proliferation growth factors that aid in HT-29 cell attachment and proliferation as a primary tumor.

One million cells were injected in a 30 μl volume into the subplanter area of the righthind footpad of the nude mice. Five days after the HT-29 cell injections, half of the mice were switched to a US17 diet containing stearidonic acid (3%.=10 g/day human equivalent dose) in place of oleic acid. The amount of primary tumor growth was measured by measuring the change in mouse footpad volume over time. Footpad volume was measured with a plethysmometer (Ugo Basile, Camerio-Varese, Italy). The results of these measurements are set forth in FIG. 12.

Figure 12:
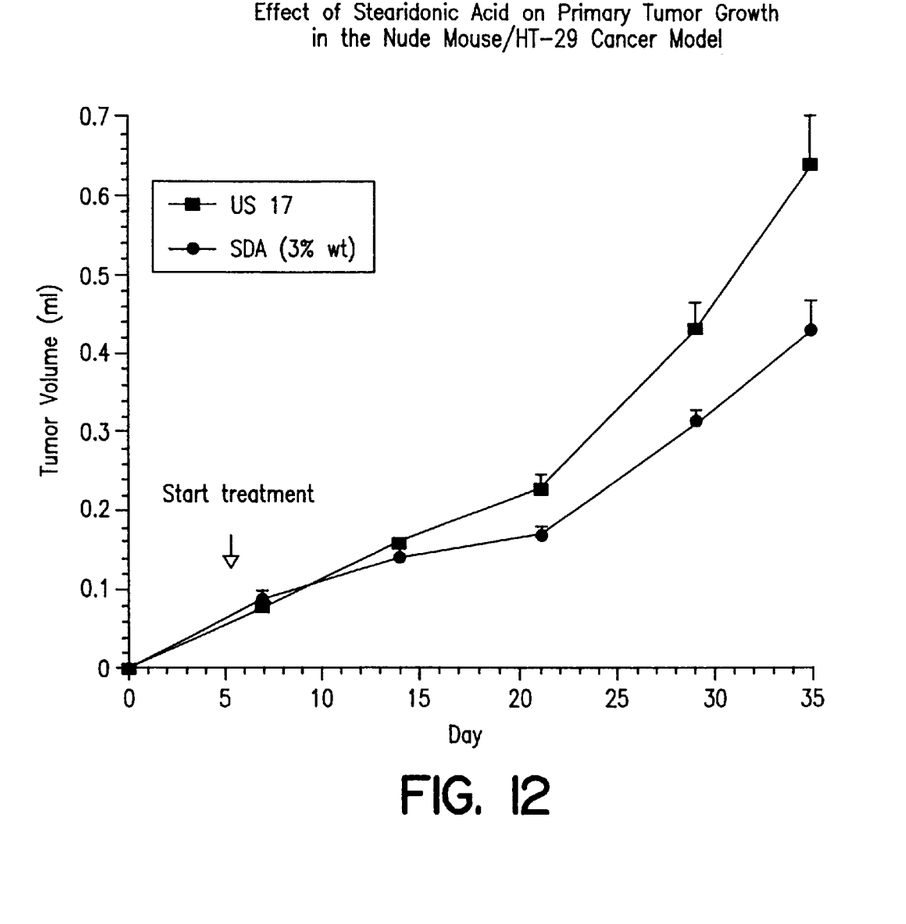
FIG. 12 illustrates the effect of SDA fed as an ethyl ester on primary tumor growth in the nude mouse/HT-29 cancer model.

FIG. 12 shows that the mice fed a US17 diet containing stearidonic acid exhibited decreased primary tumor growth as compared to those fed the US17 control diet. After 35 days, the mice fed the US17 diet containing SDA exhibited 33% less primary tumor growth than those fed the US17 diet.

Other variations and modifications of this invention will be obvious to those skilled in the art. This invention is not limited, except as set forth in the claims.

What is claimed is:

1. A method for treating or preventing cancer in a mammal, said method comprising administering to a mammal in need thereof a pharmaceutical composition consisting essentially of metabolite of α-linolenic acid which is stearidonic acid (18:4 n-3), eicosatetraenoic acid (20:4 n-3), docosapentaenoic acid (22:5 n-3) or mixtures thereof.

2. A method according to claim 1, wherein said cancer is colon cancer, breast cancer, prostate cancer or lung cancer.

3. A method according to claim 1, wherein said metabolite comprises stearidonic acid (18:4 n-3).

4. A method according to claim 1, wherein said metabolite consists essentially of stearidonic acid (18:4 n-3).

5. A method according to any one of claims 1–4, wherein said metabolite is in the form of a lipid, a carboxylate salt, an ester, a triglyceride, an amide or another pharmacologically acceptable carboxylic acid derivative.

6. A method according to any one of claims 1–4, wherein said metabolite is in the form of a triglyceride.

7. A method according to any one of claims 1–4, wherein said metabolite is in the form of an ester.

8. A method according to any one of claims 1–4, wherein said metabolite is administered in a dosage amount from about 1 mg/Kg/day to about 300 mg/Kg/day.

9. A method according to claim 5, wherein said metabolite is administered in a dosage amount from about 1 mg/kg/day to about 300 mg/kg/day.

10. A method according to claim 6, wherein said metabolite is administered in a dosage amount from about 1 mg/kg/day to about 300 mg/kg/day.

11. A method according to claim 5, wherein said metabolite is administered in a dosage amount from about 10 mg/Kg/day to about 150 mg/Kg/day.

12. A method according to claim 6, wherein said metabolite is administered in a dosage amount from about 10 mg/Kg/day to about 150 mg/Kg/day.

13. A method according to claim 7, wherein said metabolite is administered in a dosage amount from about 10 mg/Kg/day to about 150 mg/Kg/day.

14. A method according to claim 8, wherein said metabolite is administered in a dosage amount from about 10 mg/Kg/day to about 150 mg/Kg/day.

15. A method for treating or preventing cancer in a mammal, said method comprising administering to a mammal in need thereof a nutritional composition consisting essentially of stearidonic acid (18:4 n-3), eicosatetraenoic acid (20:4 n-3), docosapentaenoic acid (22:5 n-3) or mixtures thereof.

16. A method for treating or preventing cancer in a mammal, said method comprising administering to a mammal in need thereof a food composition consisting essentially of a food ingredient and stearidonic acid (18:4 n-3), eicosatetraenoic acid (20:4 n-3), docosapentaenoic acid (22:5 n-3) or mixtures thereof.

17. The method according to claim 3, wherein stearidonic acid is metabolized to long chain n-3 polyunsaturated fatty acids at a faster rate than α-linolenic acid.

18. The method according to claim 17, wherein stearidonic acid is metabolized to eicosapentaenoic acid at a faster rate than α-linolenic acid.

19. The method according to claim 17, wherein stearidonic acid is metabolized to docosahexaenoic acid at a faster rate than α-linolenic acid.

20. The method according to claim 17, wherein stearidonic acid is metabolized at a faster rate than α-linolenic to fatty acid intermediates selected from the group consisting of 20:4 n-3, 22:5 n-3 and 24:5 n-3.

21. The method according to claim 3, wherein at least 24% of stearidonic acid is metabolized to eicosapentaenoic acid.

22. The method according to claim 3, wherein at least 3% of stearidonic acid is metabolized to docosahexaenoic acid.

23. The method according to claim 17, wherein stearidonic acid is metabolized to n-3 polyunsaturated fatty acids at a faster in vivo rate than α-linolenic acid.

* * * * *

UNITED STATES PATENT AND TRADEMARK OFFICE
CERTIFICATE OF CORRECTION

PATENT NO. : 6,340,705 B1  Page 1 of 1
DATED : January 22, 2002
INVENTOR(S) : Obukowicz et al.

It is certified that error appears in the above-identified patent and that said Letters Patent is hereby corrected as shown below:

Title page,
Item [*], Notice, should read, -- ...Subject to any disclaimer, the term of this patent is extended or adjusted under 35 U.S.C. 154 (b) by 77 days. --

Signed and Sealed this

Seventh Day of September, 2004

JON W. DUDAS
*Director of the United States Patent and Trademark Office*